United States Patent [19]

Neville, Jr. et al.

[11] 4,397,843

[45] Aug. 9, 1983

[54] MANNOSE-6-PHOSPHATE-LOW DENSITY PROTEIN REAGENT EFFECTIVE AGAINST HYPERCHOLESTEROLEMIA

[75] Inventors: David M. Neville, Jr., Bethesda; Richard J. Youle, Kensington; Gary J. Murray, Bethesda, all of Md.

[73] Assignee: The United States of America as represented by the Department of Health and Human Services, Washington, D.C.

[21] Appl. No.: 341,572

[22] Filed: Jan. 21, 1982

Related U.S. Application Data

[63] Continuation-in-part of Ser. No. 199,781, Oct. 23, 1980, Pat. No. 4,356,117.

[51] Int. Cl.³ ............................................. A61K 37/00
[52] U.S. Cl. ................................ 424/177; 260/112 R; 435/240; 435/241
[58] Field of Search .................... 424/177; 260/112 R; 435/240, 241

[56] References Cited

PUBLICATIONS onin et al.-Chem. Abst., vol. 89, (1978), p. 1790g.

*Primary Examiner*—Sam Rosen
*Attorney, Agent, or Firm*—John S. Roberts, Jr.

[57] ABSTRACT

A new reagent effective in inhibiting cholesterol synthesis 75% in human fibroblasts derived from patients suffering from the disease familial hypercholestrolemia is Man6P-low density lipoprotein and is effective in tissue culture test systems at 100 µg/ml after a ten-hour exposure. The broad purpose of this invention is to modify the receptor specificity of a protein so that it will enter cells which were previously impermeable and exert new effects or reverse a pathological condition. That is, the compound of this invention is a useful reagent in the selective cytotoxic treatment of hypercholesterolemia.

2 Claims, 2 Drawing Figures

MANNOSE-6-PHOSPHATE-LOW DENSITY PROTEIN REAGENT EFFECTIVE AGAINST HYPERCHOLESTEROLEMIA

This is a continuation-in-part application of Ser. No. 199,781 filed Oct. 23, 1980 now U.S. Pat. No. 4,356,117.

This invention relates to a new reagent effective in inhibiting cholesterol synthesis 75% in human fibroblasts derived from patients suffering from the disease familial hypercholestrolemia is Man6P-low density lipoprotein and is effective in tissue culture test systems at 100 μg/ml after a ten-hour exposure. The broad purpose of this invention is to modify the receptor specificity of a protein so that it will enter cells which were previously impermeable and exert new effects or reverse a pathological condition. Toxins may also be modified in this manner producing cell type specific and tumor suppressive reagents which are effective in a dose range of 0.3-3 μg. The object here is to use the reagent to selectively kill one cell type which is exerting a pathological effect without affecting normal cells. Among others to which this invention is applicable are Man6P-low density lipoprotein, Man6P-ricin, Man6P-Modeccin, anti Thy 1.2 monoclonal antibody-ricin and anti Thy 1.1 monoclonal antibody-ricin.

The purpose of this invention is to modify the receptor specificity of a potent toxin by coupling it with a monoclonal antibody directed at a specific tumor or differentiation antigen. The object generally is to use this reagent to selectively kill human tumor cells without affecting normal cells.

A number of attempts have been made to develop tumor specific cytotoxic reagents by coupling antitumor antibodies to toxins. Early studies failed to show large selectivity between tumor cells and normal cells because (1) toxin binding to normal cells via toxin B chain was not blocked and (2) polyclonal antibodies raised in xenogenic animals have broad specificity and react with normal cells (Science, 169:68–70, 1970; J. Natl. Cancer Inst., 55:473–477, 1975; Nature, 271:752–755, 1978).

These antibody toxin conjugates use the entire toxin since it is shown that the toxin B chain contains a necessary entry function in addition to its usual binding function. The toxin ricin is bound to normal cells with lactose. In animal studies antibody-ricin conjugates are given intravenously in hyperosmotic lactose, sufficient to raise serum lactose to 20–30 mM. The entry function on the toxin B chain is at an intracellular site not accessible to lactose. Therefore, the entry function is maintained and the antibody toxin conjugate in the presence of lactose has the same toxicity as ricin alone toward the target cell. To insure a high degree of tumor specific selectivity, antibodies are of monoclonal origin.

As to tumor suppressant composition used i.v. at Day 1, it has been found that an amount of 1–3 μg of anti Thy monoclonal antibody-ricin is a preferred dosage.

Use Statement

The first purpose of this invention is to modify the receptor specificity of a physiologic protein with the object that the protein may gain entrance to cells which have lost their normal receptor-mediated uptake through a disease process. The new receptor entry route is chosen so that the protein exerts its normal physiologic effect through the altered receptor-uptake process. Thus mannose-6-phosphate-low density lipoprotein enters familial hypercholesterolemic fibroblasts through the mannose-6-phosphate and down regulation of the rate limiting enzyme in cholesterol synthesis is acheived. This, in turn, through feedback mechanisms, may lower the elevated levels of low density lipoprotein in patients suffering from familial hypercholesterolemia.

The reagent of this invention is effective in inhibiting cholesterol synthesis by 75% in human fibroblasts derived from patients suffering from familial hypercholesterolemia, Man6P-low density lipoprotein, and is effective in tissue culture tests at 100 μg/ml.

The second purpose of this invention is to modify the receptor specificity of a toxin with the objective that the toxin will now bind, enter and kill a specific population of cells while leaving other cells unaffected. Thus, mannose-6-phosphate ricin in the presence of lactose selectively kills human fibroblasts while other cell types are unaffected. Monoclonal antibody toxin hybrids behave in a similar fashion.

This invention is a test or kit with some human useful linkage which utilizes an antibody toxin conjugate where the entire toxin is utilized and it is shown that the toxin B chain contains a necessary entry function in addition to its usual binding function. In animal studies antibody ricin conjugates are given intravenously in hyperosmotic lactose sufficient to raise the serum lactose to 20–30 mM.

Prior Art Statement

Low density lipoprotein has been modified by incorporation of cationic groups and enters familial hypercholesterolemic fibroblasts and down regulates the rate limiting enzyme in cholesterol synthesis. [Proc. Natl. Acad. Sci. USA, 73:3178 (1976)]. Since this modification allows low density lipoprotein to bind to many receptors on many cell types, it does not constitute a cell type specific reagent and therefore has limited potential both conceptually and practically. Previous to the present construction of mannose-6-phosphate-low density lipoprotein there was no reported method for efficiently introducing functional proteins into specific cells.

The following articles describe the introduction of proteins into cell via alternate receptors. However, the internalized proteins did not affect the cell and the aim was not to achieve a functional protein operating inside the cell.

Biochem. Biophys. Res. Commun., 45:622–628, 1971.

J. Biol. Chem., 253:6107–6110, 1978.

The following articles were attempts to create cell type specific toxins by coupling toxin A chains with hormones. Toxicity when present was too low to be practical.

J. Biol. Chem., 252:1505–1514, 1977.

J. Biol. Chem., 252:1515–1522, 1977.

J. Biol. Chem., 254:1028–1032, 1979.

The following is the first report of the use of lactose to block the ricin binding site of a hybrid toxin and the first report of intravenous infusions of lactose protecting mice from ricin toxicity.

J. Exp. Med., 143:1461–1474, 1976.

Brit. J. Cancer, 34:418–425, 1976.

In the case of M6P-ricin and anti Thy 1.2 ricin hybrids, which contain the ricin B chain, these hybrids require the presence of lactose to block the ricin B chain binding to achieve cell type specificity. This limits the presently achievable selectivity between cell types to between 30- and 700-fold. Naturally occurring toxins which utilize receptor mediated protein transport systems can exhibit cell type selectivities up to 10,000-fold. This degree of selectivity could in principle be also reached by antibody-toxin hybrids of the proper construction. The currently available selectivity, however, is more than ample for the use of hybrids as selective agents for the isolation of receptor minus mutant cell lines. It may be possible to efficiently select for variants that lack any cell surface components toward which an antibody can be raised. This approach avoids utilization of complement dependent cell lysis.

The use of monoclonal antibodies as the cell recognition moiety of toxin hybrids greatly expands the possible uses of antibody-toxin hybrids. Several cell-type specific and tumor specific or tumor associated monoclonal antibodies have been produced. Hybrids of ricin with these antibodies would kill the antigen bearing cells selectively. There is considerable scientific and pharmacologic potential for these potent monoclonal antibody-ricin hybrids as cell type and tumor specific toxins.

Autoimmune Diseases

Ricin coupled to an antigen will bind, enter and kill the specific B and T cell clones which make and regulate antibody directed toward this antigen. This will constitute a specific cure for autoimmune diseases such as myesthemia gravis, lupus erythematosus, rheumatoid arthritis, etc. Where the antigen in question is known and can be purified such as the acetylcholine receptor for myesthemia gravis, it only remains to couple the antigen to ricin and then to administer intravenously to the patient in the presence of hyperosmotic lactose sufficient to raise blood lactose to 20-30 mM. In autoimmune diseases where the antigen is unknown, such as rheumatoid arthritis, the antigen must be identified and then purified.

In retrospect, the first purpose of this invention is to modify the receptor specificity of a physiologic protein with the object that the protein may gain entrance to cells which have lost their normal receptor-mediated uptake through a disease process. The new receptor entry route is chosen so that the protein exerts its normal physiologic effect through the altered receptor-uptake process. Thus, mannose-6-phosphate-low density lipoprotein enters familial hypercholesterolemic fibroblasts through the mannose-6-phosphate receptor and down regulation of the rate limiting enzyme in cholesterol synthesis is achieved. This, in turn, through feedback mechanisms, may lower the elevated levels of low density lipoprotein in patients suffering from familial hypercholesterolemia.

The second purpose of this invention is to modify the receptor specificity of a toxin with the objective that the toxin will now bind, enter and kill a specific population of cells while leaving other cells unaffected. Thus, mannose-6-phosphate ricin in the presence of lactose selectively kills human fibroblasts while other cell types are unaffected. Anti Thy 1.2-ricin also specifically kills cells carrying the Thy 1.2 antigen while leaving other cells unaffected. This reagent is active against tumors carrying Thy 1.2.

The tumor suppressive composition is active against lymphoma consisting of an injection of hybrid protein anti Thy 1.2 monoclonal antibody-ricin and hyperosmotic lactose. The inoculation i.v. of murine tissues in vivo by lymphoma is made at −20 to −25 days and the tumor suppressant composition is used i.v. at Day 1 in an amount of 1-3 μg of anti Thy monoclonal antibody-ricin together with sufficient hyperosmotic lactose to raise the lactose level to 20-30 mM. The broad purpose of this invention is to modify the receptor specificity of a potent toxin such as ricin by coupling it with a monoclonal antibody directed at a specific tumor or differentiation antigen. The object here is to use the reagent to selectively kill tumor cells without affecting normal cells.

Figure 1:
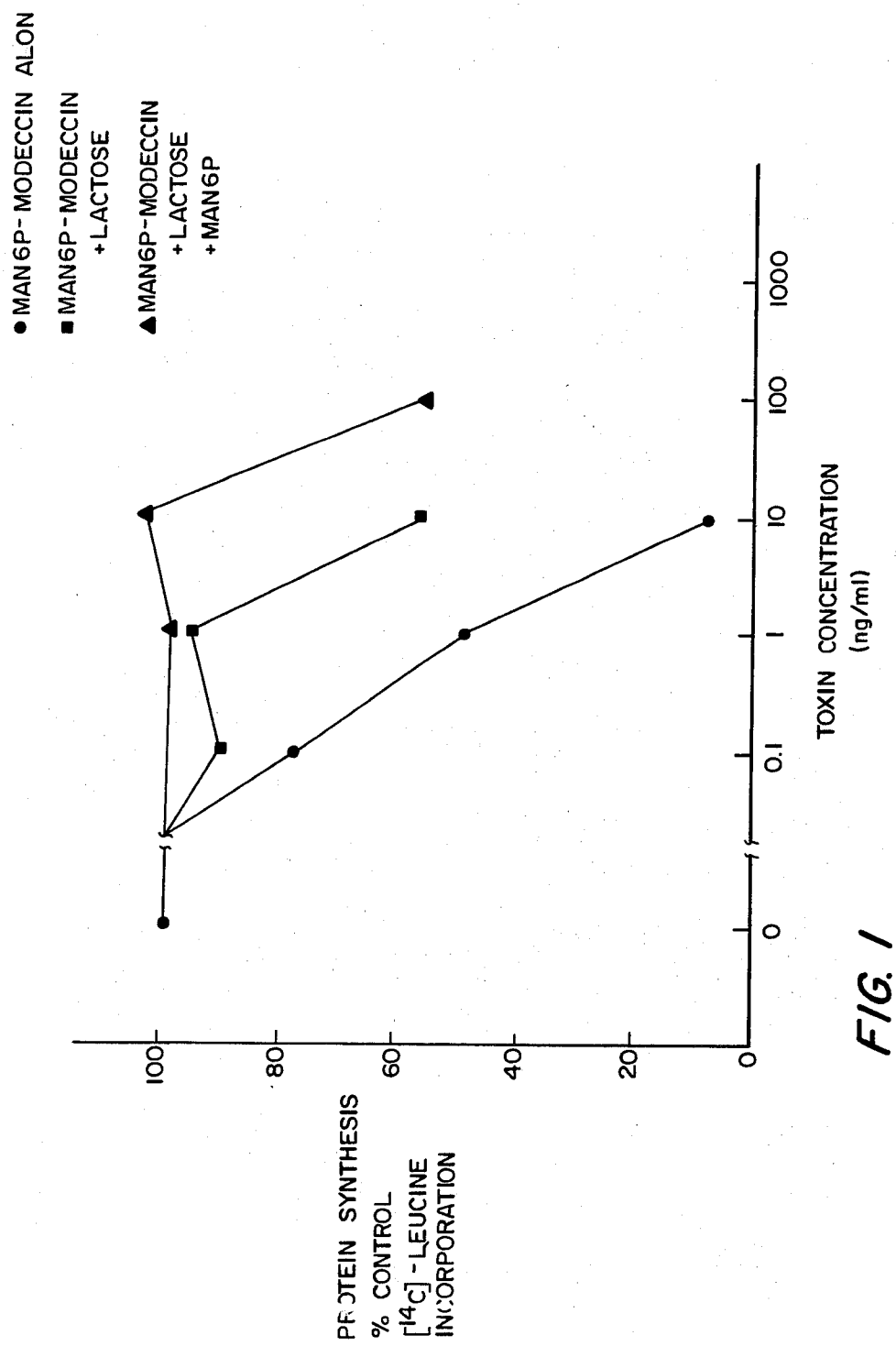
FIG. 1 demonstrates the toxicity of the Man6P-Modeccin via the gal route of entry (●—●), the Man6P route (■—■) and a non-specific route (▲— ◀).
Figure 2:
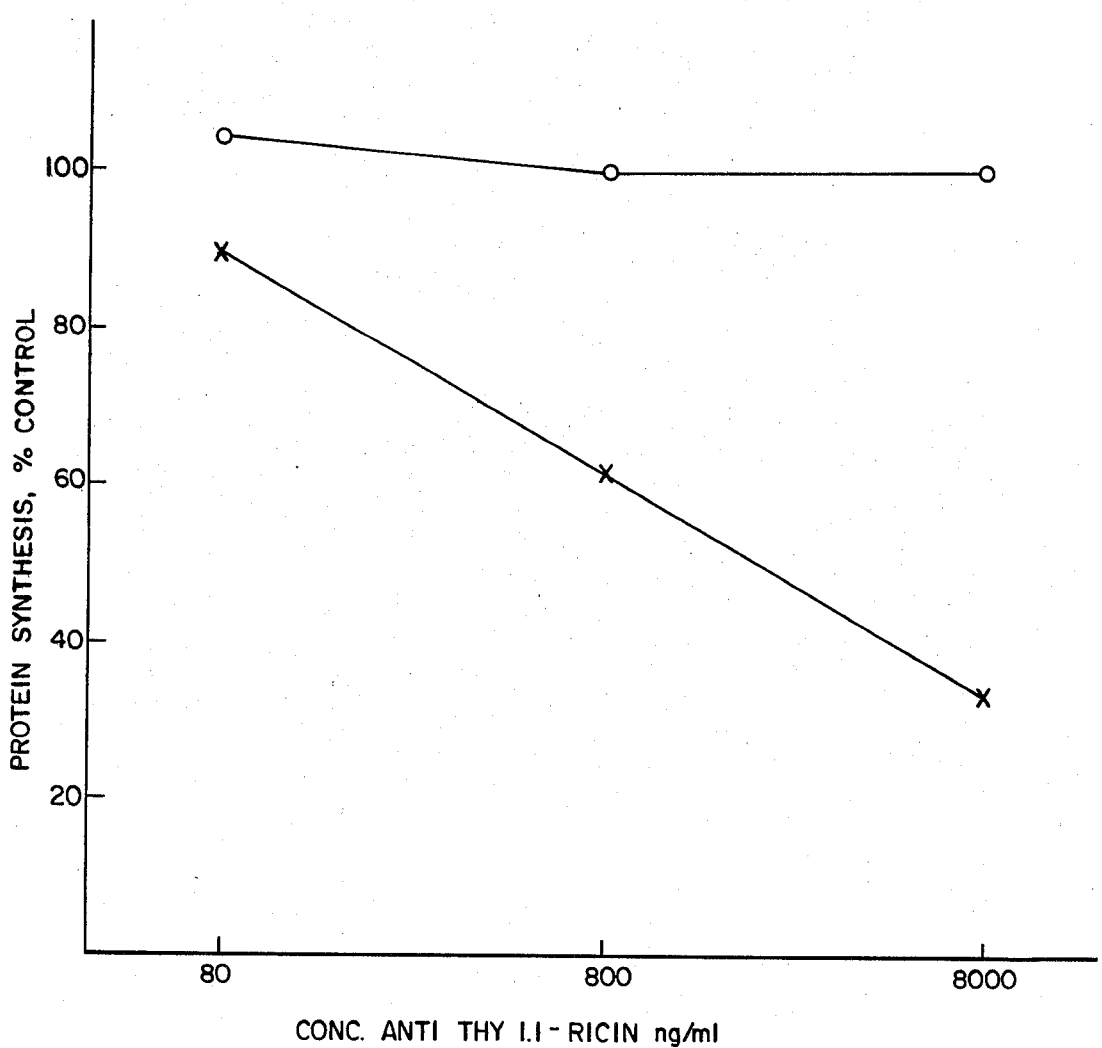
FIG. 2 demonstrates the effect of anti Thy 1.1 monoclonal antibody-ricin on the inhibition of protein synthesis on AKR-SL2 and EL-4 cells. Protein synthesis is inhibited in AKR-SL2 cells which carry the Thy 1.1 antigen. No effect is seen in this concentration range on EL-4 cells which lack the Thy 1.1 antigen. This demonstrates the cell type specificity of this reagent.

AKR-SL2 cells and EL-4 cells both $1 \times 10^6$ cells/ml were incubated in 1 ml aliquots with different doses of hybrid and 0.07 M lactose. After three hours $^{14}$C-Leucine was added to measure the rate of protein synthesis for the next 1.5 hours. The cells were then assayed and processed.

EXAMPLE 1

Preparation of a New Toxic Hybrid: Man6P-Modeccin

Man6P-Modeccin was prepared by covalently coupling the toxic Modeccin to ω-(6-phospho)-pentamannose. The incubation mixture consisted of: 100 μl Modeccin (3 mg/ml), 100 μl ω-(6-phospho)-pentamannose (pH 8.5, 400 mg/ml), 17 μl Bicine buffer (1-N,N-bis-hydroxy-2-ethylglycine; Calbiochem) (1.5 M, pH 9.0) and 12.5 μl [$^3$H]-NaCNBH$_3$. After 40 hours at 37° C. the mixture was passed over a column of Sephadex G-25 Superfine (0.5×25 cm) and eluted with Dulbecco's phosphate buffered saline (6.7 mM Na$_2$HPO$_4$, 15 mM NaCl) (pH 7.4). Incorporation of tritium label revealed 7P (Man)$_5$ residues incorporated per mole of protein.

Toxicity of the Man6P-Modeccin preparation was assayed in the absence and presence of lactose and in the presence of lactose plus Man6P. The accompanying figure demonstrates the toxicity via the gal route of entry (●—●), the Man6P route (▲—▲) and a non-specific route (■—■). This is a clear demonstration of an alternate route of toxin entry via the Man6P receptor.

EXAMPLE 2

The following procedure with added monophosphopentamannose residues provide ricin with the recognition factor common to fibroblast lysosomal hydrolases and enable the modified ricin (Man6P-ricin) to bind to the fibroblast Man6P receptor and inhibit protein synthesis in the cells via this receptor. A sample preparation showing the coupling of mannose to toxins is set out below.

Preparation of Monophosphopentamannose. Phosphomannan extracted from the yeast *Hansenula holstii* NRRL Y-2448 was a generous gift from M. E. Slodki, Northern Regional Research Laboratory, Peoria, IL. Monophosphopentamannose was prepared essentially as described by M. E. Slodki in *Biochim. Biophys. Acta,* 57:525–533 (1962) and has the following structure:

P—6-Man-α-(1→3)-Man-α-(1→3)-Man-α-(1→3)-Man-α-(1→2)-Man

After hydrolysis and ethanol precipitation, the isolated $Ba^{2+}$ salt of the pentasaccharide with residual core contamination (3–5%) was applied to a column of Sephadex G-25 superfine (100×1.5 cm) and eluted with 0.1 M acetic acid. The slow-moving component was pooled and stored as lyphilized powder. Conversion to $Na^+$ salt was effected by passing a solution of $Ba^{2+}$ monophosphopentamannose over Dowex 50 ($H^+$) and then neutralizing the effluent with NaOH.

Coupling of Monophosphopentamannose and Maltotriose to Toxins. Covalent linkage of carbohydrate to toxins was accomplished by reductive amination of the Schiff base between C-1 of the reducing terminal sugar residue and a free amino group on the protein. Carbohydrates (0.2 M) were mixed with ricin (15 mg/ml) or diphtheria toxin fragment A (10 mg/ml) and $NaCNBH_3$ (159 mM) in N,N-bis-(2-hydroxyethyl)-glycine(bicine) (50 mM, pH 9) and incubated for 24 hr at 37° C. and then dialyzed at 4° C. against 10 mM Tris-HCl, pH 7.5.

The phenol/sulfuric acid method [Ashwell, *Methods Enzymol,* 8:85–95 (1966)] was used to analyze carbohydrate content. Protein concentrations were determined by the method of Lowry et al., *J. Biol. Chem.,* 193:265–275 (1951) or by ultraviolet absorption at 280 nm. The conversion factor used for $A_{280}$ of 1 mg of protein per ml was 1.18 for both ricin and diphtheria toxin fragment A.

Coupling of ω-(6-Phospho)-tetra(α1-3)mannosyl(α1-2)-mannose to Low Density Lipoprotein [Man6-P-LDL]

Coupling of the oligosaccharide to LDL was by reductive amination essentially as reported by Schwartz and Gray, *Arch. Biochem. Biophys.,* 181:542–549 (1977). To 350 μl of LDL containing approximately 9 mg of LDL was added 100 μl of $PM_5$ ($Na^+$) (40 to 45 mg), 17 μl of 1-N,N-bis-hydroxy-2-ethylglycine (bicine, final 0.05 M), and 25 μl of $NaCNBH_3$ (final, 0.06 M). The reaction was incubated at 37° C. for 40 h and then dialyzed against four changes of 1 liter of saline EDTA, pH 7.4. Glc-LDL was prepared by substituting maltotriose (final, 0.2 M) for $PM_5$. Carbohydrate analysis of the product and control LDL incubated with $NaCNBH_3$ but in the absence of exogenous carbohydrate revealed an increase of 40 to 50 $PM_5$ groups per 500,000 daltons of LDL protein or approximately to 18% of the available lysines (based on reported 57 lysine per 100,000 molecular weight apo B. $NaCNBH_3$ freshly obtained (Aldrich) was adequate to the method of Borch et al., *J. Am. Chem. Soc.,* 93:2897–2904 (1971). Ethyl acetate was substituted for ether as the solvent of choice in preparation of the dioxanate.

We claim:

1. A reagent for treating familial hypercholestrolemia comprising an effective amount of mannose-6-phosphate-low density lipoprotein.

2. A cholesterol synthesis inhibiting reagent composition comprising an effective amount of mannose-6-phosphate-low density protein.

* * * * *